(12) United States Patent
Caroll

(10) Patent No.: US 8,261,786 B2
(45) Date of Patent: Sep. 11, 2012

(54) METHOD AND APPARATUS FOR DISPENSING POWDER SAMPLES

(75) Inventor: John Caroll, Stockton on Tees (GB)

(73) Assignee: Corn Products Development, Inc., Westchester, IL (US)

( * ) Notice: Subject to any disclaimer, the term of this patent is extended or adjusted under 35 U.S.C. 154(b) by 598 days.

(21) Appl. No.: 12/377,984

(22) PCT Filed: Aug. 15, 2007

(86) PCT No.: PCT/GB2007/003118
§ 371 (c)(1),
(2), (4) Date: Apr. 6, 2009

(87) PCT Pub. No.: WO2008/020210
PCT Pub. Date: Feb. 21, 2008

(65) Prior Publication Data
US 2010/0126285 A1    May 27, 2010

(30) Foreign Application Priority Data
Aug. 18, 2006  (GB) .................................. 0616448.7

(51) Int. Cl.
*B65B 37/00* (2006.01)
(52) U.S. Cl. .............. 141/238; 141/67; 141/72; 141/237
(58) Field of Classification Search .............. 141/1, 4–8, 141/67, 71–74, 237, 238, 329
See application file for complete search history.

(56) References Cited

U.S. PATENT DOCUMENTS

| | | | |
|---|---|---|---|
| 862,231 A * | 8/1907 | Bates | 141/68 |
| 1,488,603 A | 4/1924 | Kouwenhoven | |
| 3,223,490 A | 12/1965 | Sacken et al. | |
| 3,260,285 A * | 7/1966 | Vogt | 141/8 |
| 3,306,323 A | 2/1967 | Aronson | |
| 3,650,306 A | 3/1972 | Lancaster | 141/238 |
| 3,788,370 A | 1/1974 | Hare et al. | 141/125 |
| 4,844,298 A | 7/1989 | Ohoka et al. | 222/58 |

(Continued)

FOREIGN PATENT DOCUMENTS

JP    2006162251 A    6/2006

(Continued)

OTHER PUBLICATIONS

Russian Patent and Trademark Office Agency—Inquiry of the Substantive Examination—Application No. 2009108206/05(010996) based on PCT Application No. PCT/GB2007/003118 of Aug. 15, 2007.

*Primary Examiner* — Christopher Kim
(74) *Attorney, Agent, or Firm* — DLA Piper LLP (US)

(57) ABSTRACT

Method and apparatus for parallel dispensing of powder samples is described. Powder samples are dispensed into at least two powder sample holders, each said sample holder having a through passage which preferably generally tapers from a first aperture through which powder is introduced into said passage and a second aperture through which powder, when permitted to do so, flows from said passage. The lower apertures of the sample holders are preferably sealed using a resilient film. The powder samples are dispensed by substantially simultaneously perforating the film covering each aperture and agitating the powder samples to cause them to flow from their respective sample holders. Also disclosed are a method of generating a library of powder samples and a library of powder samples.

14 Claims, 4 Drawing Sheets

U.S. PATENT DOCUMENTS

| | | | |
|---|---|---|---|
| 4,895,706 A | 1/1990 | Root | 422/102 |
| 4,905,525 A | 3/1990 | Kurfurst | 73/864.01 |
| 5,286,451 A | 2/1994 | De Silva | 422/68.1 |
| 5,561,401 A | 10/1996 | Mineo | 332/103 |
| 2002/0137199 A1 | 9/2002 | Jobin et al. | |

FOREIGN PATENT DOCUMENTS

| | | |
|---|---|---|
| WO | 99/19215 A1 | 4/1999 |
| WO | WO 99/19215 | 4/1999 |

* cited by examiner

METHOD AND APPARATUS FOR DISPENSING POWDER SAMPLES

CROSS-REFERENCE TO RELATED APPLICATIONS

This application is a §371 of International Application No. PCT/GB2007/003118, with an international filing date of Aug. 15, 2007 (WO 2008/020210 A1, published Feb. 21, 2008), which claims priority of British Patent Application No. 0616448.7, filed Aug. 18, 2006, the subject matter of which is incorporated by reference.

FIELD OF THE INVENTION

The invention relates to a method of and apparatus for dispensing powder samples for use in the preparation and analysis of materials and, in particular, for the characterisation of existing materials and the identification of new materials.

BACKGROUND OF THE INVENTION

The characterisation of materials with a view to improving or optimising formulations or to identifying new and useful compositions usually requires the performance and recordal of large numbers of experiments. The preparation of samples for such experiments is time consuming and prone through poor human performance (owing to fatigue, boredom etc in performing repetitive operations) to error in measurement of quantities of ingredients and/or recordal of volumes, weights and other details relating thereto. The nature of the ingredients themselves, for example low viscosity liquids, medium and high viscosity liquids, thixotropic liquids, powders etc, owing to the difficulty in accurately dispensing them, may compound such human-generated errors or give rise to other potential errors during the dispensation of such ingredients.

Powders, in particular, are frequently difficult to dispense accurately and repeatedly, especially when dispensed in small amounts and in parallel. Some of the difficulties that may be experienced are initiating flow of powder from a sample holder, minimising powder retention in the sample holder and, when dispensing multiple samples, initiating dispensation of the samples at the same time. The simultaneous dispensation of a number of powders into fluids may be particularly important to ensure the sample histories are as identical as it is practical to achieve. Additionally, the dispensation of powders into fluids, especially liquids, has to ensure the powders are in intimate contact with the fluid medium. With many powders, for example starches and hydrocolloids, bulk contact with liquid tends to result in the powders agglomerating in clumps with the majority of the material not being wetted out by the liquid. Consequently, it is frequently necessary to add powders to fluids incrementally.

It is an object of the present invention to provide novel methods of and apparatus for dispensing powder samples. In particular, it is a further object of the present invention to provide novel methods of and apparatus for dispensing powder samples in parallel in which one or more of the aforementioned disadvantages is/are reduced or eliminated.

SUMMARY

According to a first aspect of the present invention, a method of parallel dispensing powder samples comprises:
 a) providing at least two powder sample holders, each said sample holder having a through passage having a first aperture through which powder is introduced into said passage and a second aperture through which powder, when permitted to do so, flows from said passage;
 b) introducing powder samples into respective sample holders;
 c) aligning said second aperture of each said holder with an aperture of a respective sample receptacle; and
 d) substantially simultaneously permitting powder to flow through said second apertures whilst agitating powder samples in said passages to aid their flow therefrom into respective receptacles.

Preferably, the method comprises providing sample holders which generally taper from the first apertures to the second apertures.

Preferably, the method comprises sealing the second apertures of the sample holders prior to introduction therein of powder samples. In a preferred embodiment, the method comprises stretching resilient film over each of the apertures and retaining the film relative to the respective sample holder to seal its second aperture. In this embodiment, step d) of the method comprises perforating the film sealing each second aperture.

Preferably, the method comprises, in step d), controlling the speed of dispensation of the powder samples through said second apertures.

Preferably, the method comprises, after the powder samples have substantially flowed through the second apertures, causing a positive gas flow through said first apertures into each of the sample holders to flush any remaining powder through said second apertures thereof.

Preferably, the method comprises, during step d), directing positive gas flows externally of said second apertures whereby sticking of powder to external surfaces of the sample holders in the vicinity of the second apertures thereof is reduced.

According to a second aspect of the present invention, apparatus for parallel dispensing powder samples comprises at least two sample holder for containing powder samples, each said sample holder having a through passage having a first aperture through which a powder sample is introduced into said passage and a second aperture through which a powder sample flows from said passage, respective flow control means for controlling flow of powder through each said second aperture and agitator means for agitating a powder sample in each said sample holder during use thereof.

Preferably, each through passage of each sample holder generally tapers from the first aperture to the second aperture thereof.

Preferably, more than two, more typically eight or twenty four, samples holders are provided. The sample holders may be integral with one another, for example a well plate having tapering through passages. Alternatively, and more preferably, the sample holders may be individual holders which are beatable in through passages in a well plate. Preferably, the sample holders may be locked in said through passages in the well plate to ensure they are positively retained therein.

A wall of each sample holder defining the through passage thereof preferably defines a volume that is frustoconical in shape. When each sample holder is an individual sample holder, preferably at least a portion of the external wall thereof is of a configuration, preferably substantially cylindrical, such that it is a close fit in a corresponding through passage in the well plate. Preferably, a lower portion of each sample holder has an external configuration that substantially parallels the internal wall shape of the sample holder defining the through passage thereof.

The flow control means associated with each sample holder may be a valve mechanism, for example an iris valve or a trapdoor type of valve or a sliding closure that slides relative to the second aperture of the sample holder. More preferably, the flow control means comprises a perforable film, for example a metal foil or, more especially, a resilient film of latex or similar material, held in clamped relationship with each sample holder to close the second aperture thereof. Separate perforators may be provided to perforate each film to open the respective apertures substantially simultaneously for powder flow therethrough. Alternatively, and more preferably, agitator means are associated with each sample holder as is described in more detail below, each agitator means being movable axially in parallel through the respective passage of each sample holder to perforate each film to open the respective apertures for powder flow.

In one embodiment, the agitator means may comprise means for physically vibrating the sample holders and powder contained therein during use. Alternatively, the agitator means may comprise an ultrasonic sound generator for vibrating the sample holders and powder contained therein during use.

More preferably, each agitator means comprises a stirrer mechanism, the stirrer mechanisms being reciprocally movable in parallel relative to the respective sample holders when the sample holders are located in their dispense positions. Preferably, the stirrer mechanisms are mounted on a common support member reciprocal movement of which relative to the dispense location of sample holders effects reciprocal movement of the stirrer mechanisms relative to the sample holders. Movement of the stirrer mechanisms towards the sample holders inserts each stirrer mechanism substantially coaxially in the respective passages of the sample holders through said first apertures thereof and, if the second apertures thereof are each sealed using a perforable film, sufficiently through said second apertures to perforate said films.

Each stirrer mechanism may comprise blades, either inflexible or flexible, brushes, wires or similar artefacts mounted for rotation about an axis that, in use, is substantially coaxial with the axis of the passage in the respective sample holder. Preferably, each stirrer mechanism comprises flexible members that, upon rotation about said axis, contact the wall of the passage of the respective sample holder to sweep powder therefrom.

In a preferred embodiment, the stirrer mechanism comprises at least one spring wire, more preferably two spring wires, mounted on and extending axially from a distal end thereof and being located substantially in a plane including said axis for rotation thereabout. The or each wire preferably has an unstrained position in which of the free end of the wire is at a radius from said axis that is greater than the radius of the first aperture of the passage of the respective sample holder. In use, the or each wire is constrained in a strained position in which the free end of the wire is located at a radius from said axis which is less than the radius of the first aperture of the passage of the sample holder whereby the wire may be moved axially relative to the sample holder and be inserted into said passage thereof. Once in the passage of the sample holder, the constrains is removed from the wire to permit the wire to move radially outwards towards its (unstrained position and contact the wall of the passage.

The wires may be constrained by any convenient mechanism. For example, each stirrer mechanism may comprise a collar mounted for reciprocal movement along said respective axis relative to said wires to engage the wires and force them radially-inwardly towards said respective axis or to disengage from the wires to permit them to return to their unstrained position. Preferably, the ends of the collars contact the wires each have an internal chamfered annular surface that engages the wires.

In a preferred embodiment, the constraint mechanism comprises a pair of parallel plates each having a number of apertures, preferably generally diamond shaped, corresponding to the numbers of stirrer mechanisms, the plates being positioned relative to the stirrer mechanisms such that their planes are normal to the axes of the stirrer mechanisms and, when the apertures of the plates are in registration with one another, the centres of the apertures are located substantially coaxially with the respective axes of the stirrer mechanisms. The plates are movable relative to one another between a first position, in which the apertures therein are in registration with one another and in which the wires of the stirrer mechanisms are in their unstrained position, and a second position, in which the apertures therein are only in partial registration with one another, and in which the wires of the stirrer mechanisms are constrained in their strained position. Preferably, both plates are movable symmetrically with respect to the axes of the stirrer mechanisms. The plates may be moved by any convenient mechanism, for example pneumatic actuators. Preferably, the plates, in their first position, are also movable axially of the stirrer mechanisms to a position remote from the distal ends thereof.

Preferably, the speed of rotation of stirrer mechanisms and/or vertical reciprocating movement of the stirrer mechanisms relative to the sample holder location are controllable to enable the rate of dispensation of the powder samples from the sample holders to be controlled.

Preferably, also the size of said second aperture of each sample holder is selected in dependence on the weight of the powder samples under consideration. Consequently, a small weight of powder sample will be matched by a small diameter of second aperture and vice versa.

The stirrer mechanisms are rotated by any convenient drive mechanism, for example a motor and belt-driven pulley system or a motor and gears system or combination of a motor, gears and belt-driven pulley system. Preferably, the drive mechanism is mounted on the common support member for the stirrer mechanisms.

Preferably, the common support member is mounted on an XYZ robot system for automated movement relative to a workstation at which, in use, the sample holders, or the well plate containing the sample holders, are located. Similarly, it is preferred that the plates of the constraint mechanism are mounted on the XYZ robot for axial movement relative to the stirrer mechanisms.

Preferably, the workstation also accommodates a sample receptacle well plate. Although the sample receptacle well plate may provide integral sample receptacles formed therein, it is preferred that it provides wells that accommodate sample receptacles, for example vials or similar, usually tubular, components which have an aperture or open end through which powder or other components, whether solid, liquid or gas, may be introduced into them. In use, during the dispensation of powder therein, the open ends of the vials are preferably in sealed relationship with the sample holders or with the lower surface of the well plate containing the sample holders, the open ends of the vial being in register with the second apertures of respective sample holders.

The sample holder well plate, or, alternatively, a separate plate interposable, in use, between the sample holder well plate and the vials may have gas outlets and/or inlets which communicate with the volume formed by the vial and the sample holder well plate or the separate plate whereby gas flowing into said volume, either from inlets or from the through passages in the respective sample holders, may be vented from said volume.

The inlets may be used to direct gas, which typically may be air, against the lower ends of the sample holders to prevent powder from sticking to the ends of the sample holders, especially when there is a possibility of vapour, from heated liquids contained in the vials, condensing on said lower ends.

In applications in which the powder samples are to be contacted with gaseous ingredients, the inlets and the vents may be used to ensure said volume is flushed with the gaseous ingredients and then closed to ensure said volume contains the gaseous ingredient.

In a preferred embodiment, there is provided means for providing a positive gas, typically air, flow into the sample holders via the first apertures thereof at the end of the powder dispense to flush through the second apertures thereof any powder remaining on the walls of the passages of the sample holders. Preferably, the gas flows vent through gas outlets described above. Typically, the gas flows may be provided by at least one gas manifold having nozzles to direct a gas flow into each first aperture of the sample holders. Each nozzle may be provided with a flow control means, for example a pneumatic speed restrictor, to control the flow of air into the apertures of the respective sample holders.

Preferably, the sample receptacle well plate may be cooled or heated, for example typically in the range of 5° C. to 100° C., although this may be varied depending upon the application. The powder samples may be dispensed into vials that are empty of other ingredients; alternatively, the vials may contain other solid, liquid or gaseous ingredients. The method and apparatus of the invention are particularly useful in dispensing powder samples into vials containing liquids. In a preferred embodiment, the liquids in the vials are vortexed during powder dispensation therein. Vortexing of the liquids in the vials may be achieved in any convenient manner. For example, in some applications, invasive or contact vortexing of the liquids in the vials may be possible in which instance techniques using magnetic stirrers may be employed with a magnetic flea being located in each vial. However, non-invasive or non-contact vortexing of the liquids is preferred. In that embodiment, the sample receptacle well plate is mounted for example on apparatus capable of moving it in an oscillatory manner to induce vortexing of the liquids in the vials.

Powder samples may be introduced into the sample holder(s) in any convenient manner including manually or automatically using powder dose delivery equipment such as Powdemium available from Autodose S.A., which equipment being capable of delivering specific weights of powder into the sample holder(s).

An XYZ robot system may be used to move the sample holder(s) between powder dose delivery equipment and the dispensing station. The sample holder(s) may be pre-assembled with the sample receptacle well plate.

Preferably, the robot systems of the apparatus and automatic powder dose delivery equipment are controlled by computer means. Preferably, the computer means is programmed to contain libraries of ingredients and libraries of sample compositions. The computer means is operable to deliver powder doses into the sample holders and to control the cooling/heating/vortexing of liquids in the vials in accordance with desired sample compositions.

The present invention also includes generating libraries of powder samples by preparing powder samples and dispensing the samples into sample holders and temporarily sealing the sample holders to preserve the condition of the samples and prevent contamination thereof. The invention also includes powder samples comprising at least two sample holders containing powder samples, the sample holders being temporarily sealed.

It will be appreciated the method and apparatus of the present invention may be used to generate samples for a variety of chemical systems. For example, the applications may be the dissolution of pharmaceutical actives; addition of catalysts to reaction systems; preparation of beverage and food systems where controlled dissolution is required, eg drinking chocolate; and adhesive and building coatings where powder ingredients are to prepare a formulation.

One particular application for which it is particularly suited is the examination of starch and hydrocolloids wherein it is necessary to prepare samples of starches and hydrocolloids in water are prepared to enable gelling, viscosity, colour, clarity and other properties to be investigated. The preparation of starch and hydrocolloid solutions usually requires the addition of the starch or hydrocolloid to water with stirring to ensure the starch or hydrocolloid is properly dispersed. If water is added to the starch or hydrocolloid powder, good dispersion is not usually achieved as the powder tends to clump together in agglomerates. Additionally, when comparing large numbers of starches, hydrocolloids and mixtures of starches and hydrocolloids, it is preferably that the experimental histories of the samples are as uniform as it is practical to achieve.

Using the method and apparatus according to the invention, powder samples comprising amounts of starches, emulsifiers, encapsulants, sugars and flours in the range 2 mg to 1000 mg have been successfully dispensed into vials frequently with a residual powder level of less than 5%, more particularly less than 3%, of the target weight remaining in the sample holders.

BRIEF DESCRIPTION OF DRAWINGS

The invention will now be illustrated by reference to the accompanying drawings.

DETAILED DESCRIPTION

Figure 1:
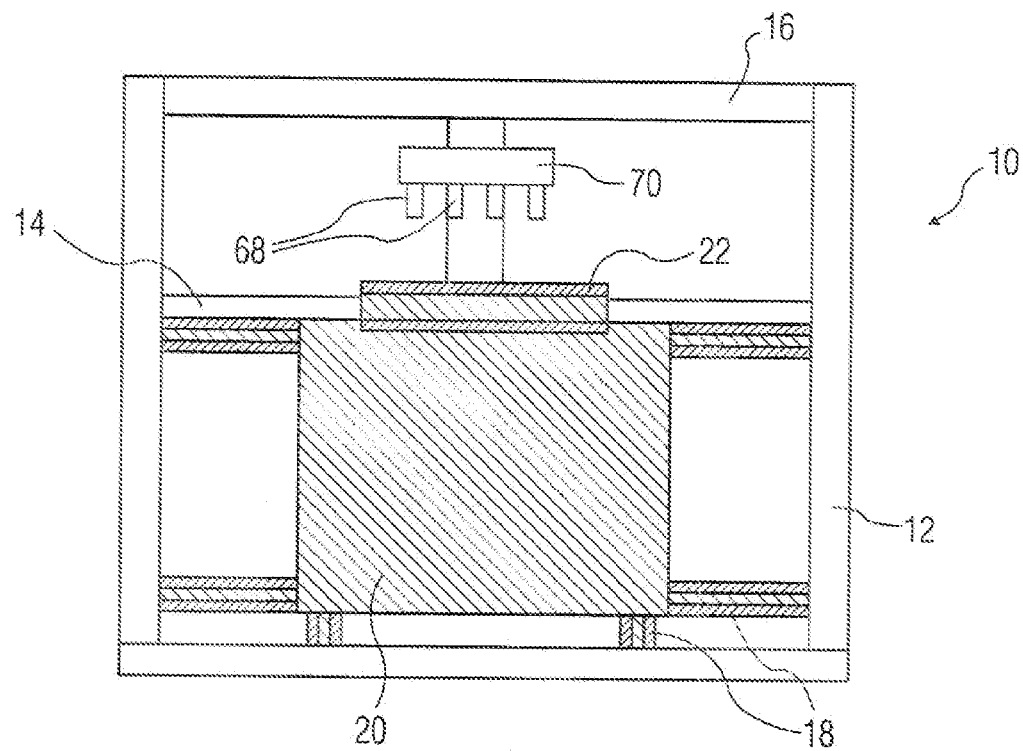
FIG. 1 is a schematic plan view of apparatus according to the invention.

Referring to the drawings, a powder dispensation apparatus 10 is shown. The apparatus 10 is described in terms of handling eight samples simultaneously. However, it will be appreciated that less samples or other, higher, numbers of samples, eg twenty four, may be also be handled by the apparatus if desired.

The apparatus 10 has a frame 12 on which is mounted a base plate 14 of an automated XYZ system 16, for example available from Tecan Limited.

Figure 4:
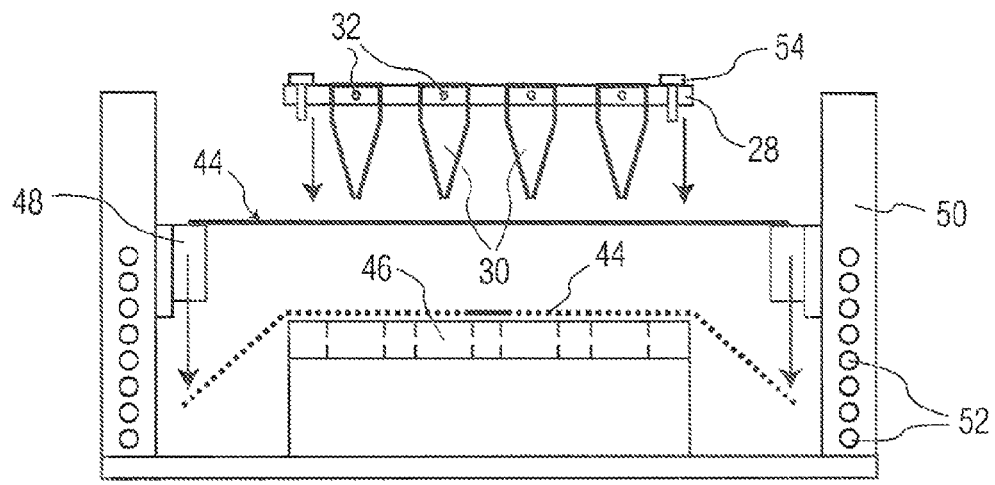
FIG. 4 is a schematic end view of sample holders being assembled with a latex film to seal the second apertures of the holders.
Figure 5:
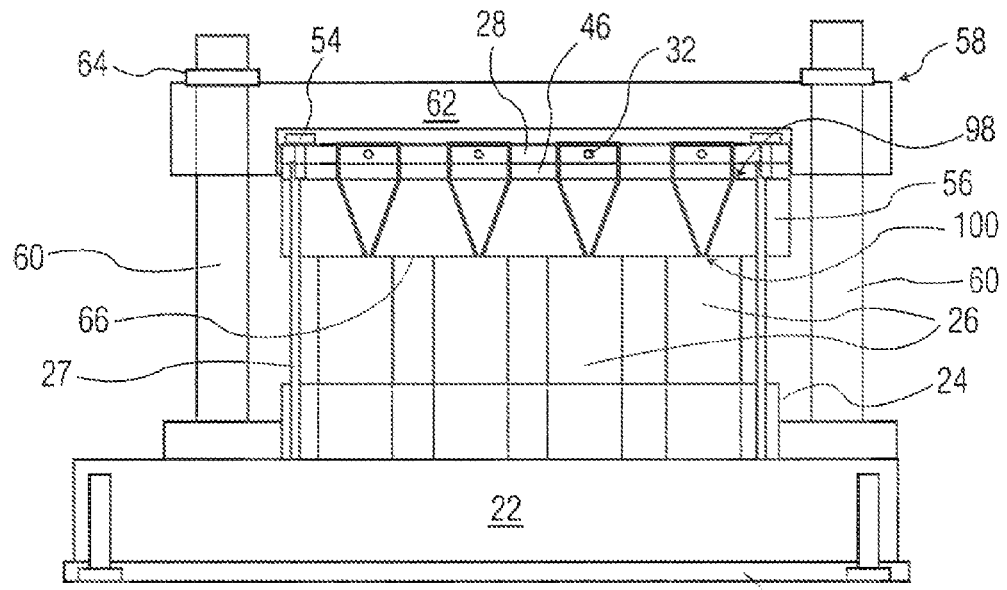
FIG. 5 is a schematic end view showing the sample holders of FIG. 4 assembled together with the sample receptacles.
Figure 6:
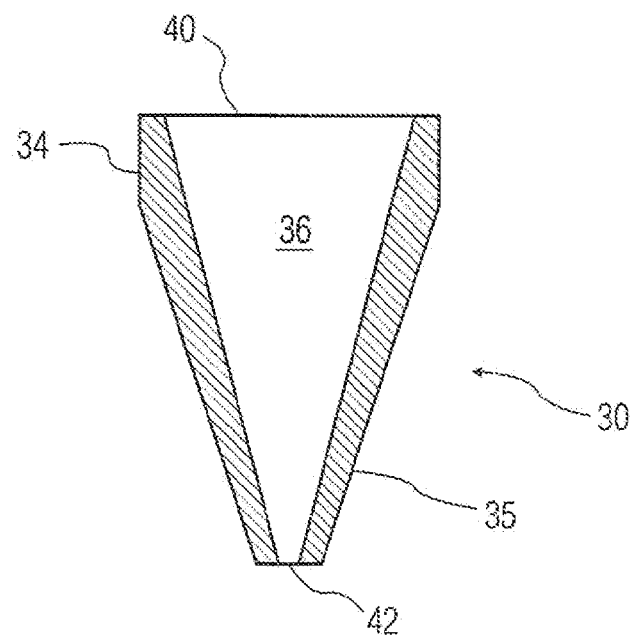
FIG. 6 is a schematic vertical cross-section through a sample holder in accordance with the invention.

Mounted on the frame 12 beneath the base plate 14 on anti-vibration mountings 18 is an orbital vortexing mechanism 20. A standard cooler/heater unit 22 is mounted on top of the vortexing mechanism 20 on which is located a sample receptacle well plate 24 for holding eight sample receptacles in the form of vials 26. The cooler/heater unit 22 is provided with location rods 27 for locating a sample holder well plate 28 relative thereto whereby sample holders 30 carried by the well plate 28 are substantially centred on the vials 26 (the well plate 28 and sample holders 30 are shown only representationally in FIG. 2 but in greater detail in FIGS. 4 to 6). The sample holder well plate 28 has eight through passages in which are located the individual sample holders 30. The through passages are cylindrical and are intersected by threaded passages in which are screwed retaining screws 32 whereby the sample holders 30 may be positively retained relative to the well plate 24.

Each sample holder 30 is essentially tubular (see FIG. 6 in particular) and has an upper substantially cylindrical external wall portion 34 which is a close fit in the respective through passage in the well plate 28 and a lower wall portion 35 which is substantially parallel to the inner wall 38 of the sample holder 30. The inner wall 38 of each sample holder 30 defines a through passage 36, the volume of space defined by the wall 38 being substantially frustoconical in shape the direction of taper of which is from the top to the bottom of the sample holder 30. A powder sample (not shown) may be introduced into the sample holder 30 through a first, upper aperture 40 and dispensed into a vial through a second, lower aperture 42.

Figure 2:
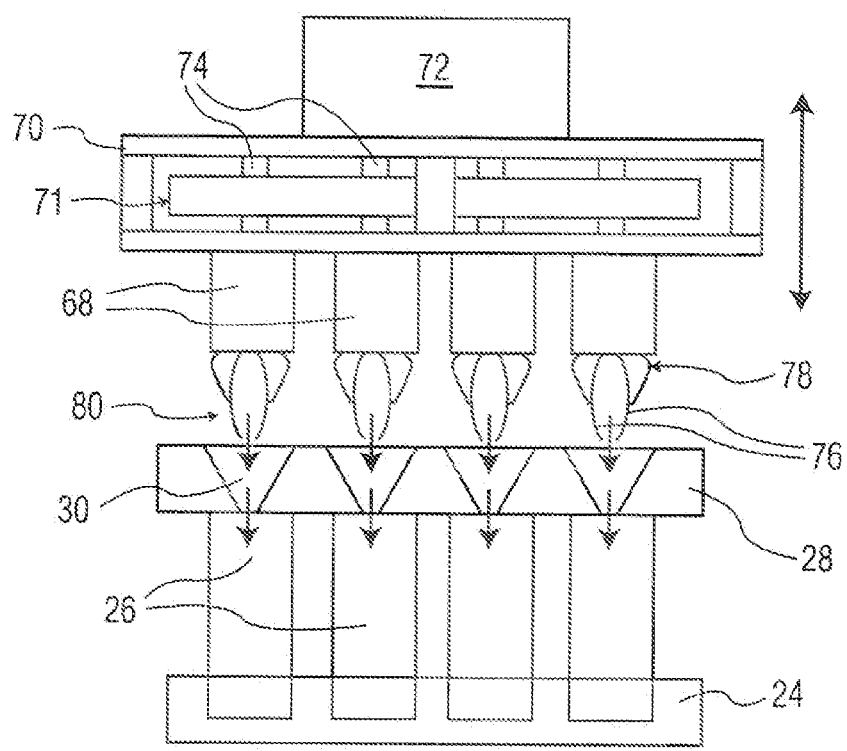
FIG. 2 is a schematic end view of part of the apparatus in greater detail.

As depicted by the small arrows in FIG. 2, after the powder samples have substantially flowed through the second apertures 42, a positive gas flow may be caused to flow through the first aperture 40 into each of the sample holders 30. Arrows in FIG. 2 also illustrate the direction of gas flow externally of the second apertures 42.

Figure 8A:
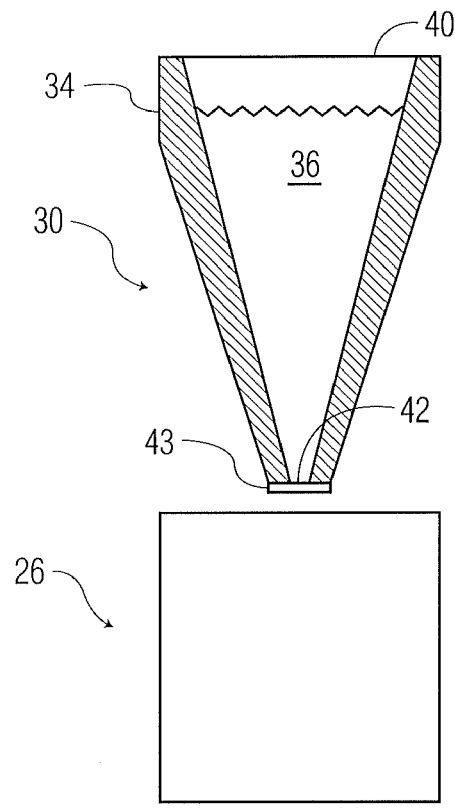
FIGS. 8A and 8B are schematic vertical cross-sections through a sample holder and receptacle.
Figure 8B:
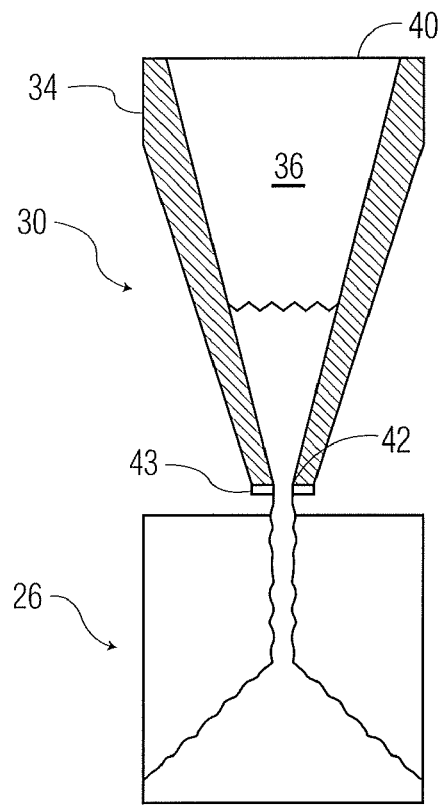

The flow of powder from the through passage 36 through second aperture 42 of the sample holder 30 is controlled by a flow control means 43. The flow control means may be a valve mechanism (not shown) or, for example, a perforable film as shown in FIGS. 8A and 8B. The perforable film may be a metal foil retained relative to the second aperture 42 for example by an apertured clamp plate (not shown). In a preferred embodiment, the perforable film is a resilient film, for example a latex film such as Theraband™ available from Physiomed, retained relative to the second aperture 42. A latex film 44 is preferably retained relative to the sample holders 30 by being clamped between the sample holder well plate 28 and a lower apertured plate 46 (see FIG. 4). This may be achieved by clamping the latex film 44 under tension around its periphery using clamps 48 mounted for vertical movement on a frame 50 and lowering the clamps 48 to further stretch the film 44 over the lower plate 46 (as shown in dotted lines) and locking them into position using locking holes 52 in the frame 50. The sample holder well plate 28 containing the sample holders 30 is them positioned relatively to the lower plate 46 and pushed down such that the lower ends of the sample holders 30 pass through the apertures in the plate 46 to tension the film 44 even further over said lower ends of the sample holders 30 to close the apertures 42 thereof. The film 44 is then trapped between the well plate 28 and the lower plate 46 and thumb screws 54 are used to secure the well plate 28 to the lower plate 46. Excess film 44 around the periphery of the well plate 28 is then trimmed away.

The assembled well plate 28, sample holders 30 and lower plate 46, following charging of the sample holders 30 with powder samples, are assembled together with a vapour control plate 56 on the location rods 26 of the well plate 24 and clamped relative thereto using a quick clamping system 58. The clamping system 58 has two pairs vertical steel shafts 60 (only one pair shown in FIG. 5) mounted on the vortexing mechanism 20 and a pair of clamping blocks 62 (only one shown in FIG. 5) each mounted on a pair of the shafts 60. The clamping blocks 62 are retained relative to the shafts by locking mechanisms 64. In the assembled position, the lower ends of the sample holders 30 are located substantially centrally of the aperture of the vials 26.

The vapour control plate 56 has substantially cylindrical through bores (not shown) corresponding to the apertures in the well plate 28 and lower plate 46. Extending through the walls of the plate 56 are pairs of gas inlet and outlet passages, each pair of passages opening into a respective through bore in the plate 56. The gas inlet passages are positioned such that gas flowing into the bore is directed at the lower end of the sample holder located therein when the plate 56 is assembled with the well plate 28, sample holders 30 and lower plate 46. The gas outlet passages are used to vent any gas flowing into the vials or generated therein. The lower surface 66 of the plate 52 is in sealed relationship through a resilient layer (not shown), eg PTFE, with the ends of the vials 26 located in the well plate 24.

Mounted on the robot system 16 by a common member in the form of a housing 70 for a rotary drive transmission system 71 are eight agitators in the form of stirrer mechanisms 68 (see FIG. 2 in particular). The transmission system 71 is driven by an electrical stepper motor 72, for example a Vecta CSK™ 23A motor available from Oriental Motors. The transmission system may be a belt and pulley, a gear system or a combination of gears and a belt and pulley system, as desired. The stirrer mechanisms 68 are mounted on the output drive shafts 74 of the transmission system 70 for rotation about respective vertical axes. The axes are positioned such that, when the agitators are positioned over the well plate 28, they are substantially coaxial with the axes of the corresponding through passages 36 of the respective sample holders 30.

Preferred stirrer mechanisms 68 are sweepers available from Autodose S.A. Such stirrer mechanisms 68 have two diametrically-opposed spring wires 76 mounted on and extending axially from a distal end thereof, the wires 76 being located substantially in a plane including the respective axis. The wires 76 have a unstrained position (shown at 78) in which at least a part of the wires 76 are at a radius from the respective axis that is greater than the radius of the first apertures 40 of the passages 36 of the sample holders 30. In use, the wires 76 are constrained in a strained position (shown at 80) in which all of the wires 76 are at a radius from said axis which is less than the radius of the first apertures 40s of the passages 36 of the sample holders 30 whereby the stirrer mechanisms 68 together with their wires 76 may be moved axially relative to the sample holders 30 and such that the wires 76 may be inserted into the respective passages 36 of the sample holders 30. Once in the passages 36 of the sample holders 40, the constraint is removed from the wires 76 to permit the wires 76 to move towards their unstrained position 78 and contact the walls 38 of the passages 36.

The wires 76 may be constrained by any convenient mechanism. For example, the mechanism may comprise a collar (not shown) mounted for reciprocal movement along said axis relative to said wires to engage the wires 76 and force them radially-inwardly towards said axis or to disengage from the wires to permit them to return to their unstrained position. Preferably, the end of the collar contact the wires has an internal chamfered annular surface that engages the wires.

Figure 3:
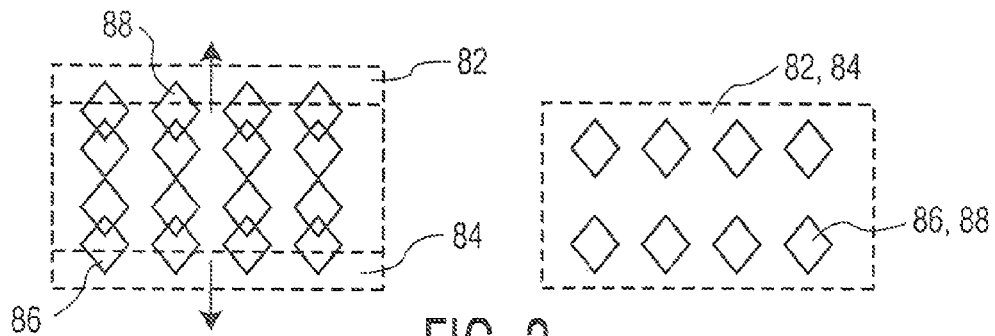
FIG. 3 is a schematic view of the two apertured plates used to constrain the wires of the stirrer mechanisms shown in FIGS. 1 and 2, the two plates being shown in register with one another on the right hand side of the figure and not in register with one another on the left hand side of the figure.

In an alternative, preferred embodiment, a pair of apertured plates 82, 84 (see FIG. 3) are mounted on a frame (not shown) which, in turn, is mounted on the robot system 16 by a pneumatic actuator (not shown). The plates 82, 84 are mounted parallel to one another with their planes normal to the vertical axes of the stirrer mechanisms 68 and each has eight apertures 86, 88, preferably diamond shaped, which are centred on the vertical axes of the stirrer mechanisms 68. The plates 82, 84, in register with one another so that the apertures 86, 88 are aligned with one another (see right hand side of FIG. 3) are vertically movable by the pneumatic actuator between first position in which the planes of the plates 82, 84 intersect the bodies of the stirrer mechanisms 68 and a second position in which the planes of the plates 82, 84 intersect the wires 76 of the stirrer mechanisms 68 at the point of largest ratio of the wires 76 relative to their respective axes. In the second position, the plates 82, 84 are movable relative to the frame using for example pneumatic actuators (not shown) normal to the vertical axes of the stirrer mechanism but in opposite directions to one another by equal amounts such that the apertures 86, 88 are moved to positions in which they are only in partial registration with one another (see left hand side of FIG. 3) thereby moving the wires 76 into their constrained position 80.

Figure 7:
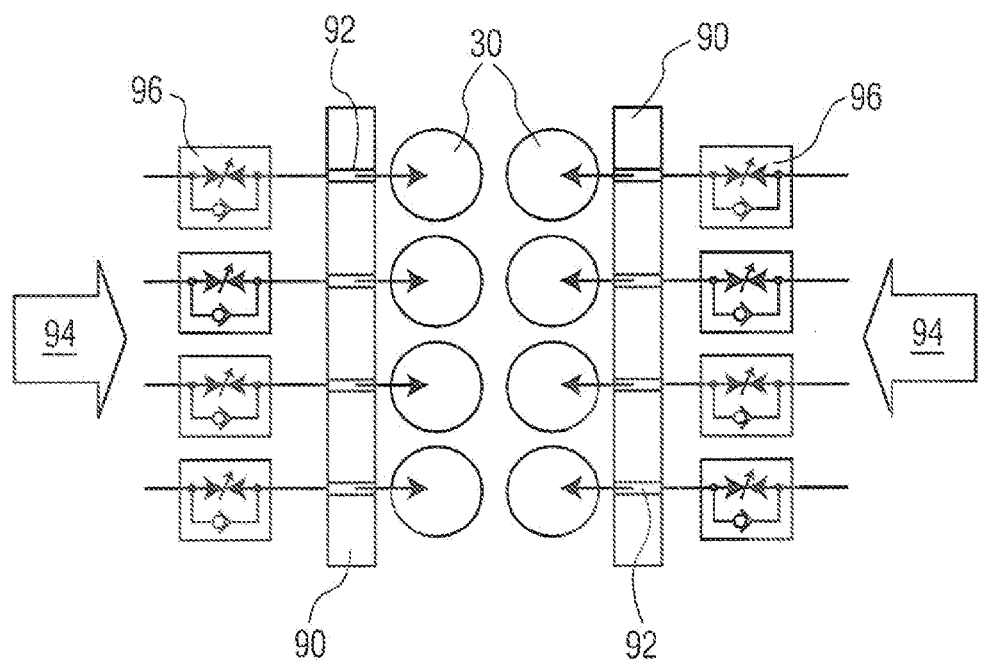
FIG. 7 is a schematic plan view of an air blast delivery system.

Also mounted on the housing 70 are two nozzle bars 90 each located parallel to four of the sample holders 30 and each having four nozzles 92, one for each adjacent sample holder 30. Gas, typically air, from a common manifold (indicated by arrows 94) is fed to the nozzles 92 via individual pneumatic speed restrictors 96 and then into the sample holders 30 to provided a positive gas flow (indicated by small arrows in FIG. 7) into the holders 30.

A computer (not shown) is used to control operation of the robot system 16.

In use, a sample receptacle well plate 24 is charged with eight vials 26 into which liquid and such other ingredients that may be required have been charged. The vials 26 may be prepared manually or, alternatively, using automated dosing equipment (not shown) under the guidance of the computer or a separate computer that is preferably in communication with the first computer. If desired, the vials 26 may be weighed between each addition of ingredients to ensure the ingredient recipes are being followed and the actual quantities of ingredients are known and recorded.

The sample holder well plate 38 is assembled separately, as described above in relation to FIG. 4. The sample holders 30 in assembly of the well plate 28, sample holders 30 and lower plate 46 are then each charged with a powder sample. The charging of the sample holders 30 may be done manually but is more preferably done automatically using an autodosing machine (not shown), for example an MTM2000™ available from Autodose S.A. Preferably, the weight of the powder sample for each sample holder 28 is recorded by the computer.

The well plate 24, together with the vials 26 is located on the ESS unit 22 and the vapour control plate 56 is positioned over it on the locating rods 27 to rest on the tops of the vials. The assembly of the well plate 28, sample holders 30 and lower plate 46 is then positioned on the locating rods 27 to rest on the vapour control plate 56. The clamping blocks 62 are then slid down their respective pairs of shafts 60 into engagement with the thumb screws 54 and locked into position using the locking mechanisms 64 to clamp the whole assembly together.

The cooler/heater unit 22 is then operated by the computer to equilibrate the temperature of the contents of the vials at the required levels and, if desired, gas flows may be introduced by and vented from the regions of the lower ends of the sample holders 30 to reduce the potential for fluid condensing thereon by gas inlet means 98 and gas outlet means 100. The vortexing mechanism 20 is then operated by the computer to induce vortexing of the liquids in the vials. Once the experimental environmental conditions have been achieved, housing 70 is lowered to insert the stirrer mechanisms 68 into the respective sample holders 30. The plates 82, 84 are then moved into register with one another to permit the wires 76 of the stirrer mechanisms 68 to move to their unconstrained positions 78. The plates are then moved vertically upward so that they are clear of the wires 76. In this position of the stirrer mechanisms, if more than one powder has been added to the sample holders 30, the stirrer mechanisms 68 may be operated to impart a mixing action to the powder samples in the sample holders 30.

The stirrer mechanisms 68 are then moved axially lower to enable the wires 76 thereof and perforate the latex film sealing the second apertures 42 of the sample holders 30, the latex film snapping away from the apertures 42. The stirrer mechanisms 68 are then withdrawn slightly and operated to stir the powder samples to cause them to flow through the apertures 42 into the respective vials 26. The speed of dispensation of the powder samples from the sample holders 30 may be controlled by controlling the speed of rotation of the wires 76 and/or reciprocating the stirrer mechanisms 68 vertically relative to the sample holder location. When substantially all of the powder samples have transferred to the respective vials, a short air flow is initiated through the nozzles 92 into each sample holder to flush through any remaining particles of the powder samples.

The use of a resilient film 44 as a valve mechanism results in an effectively instantaneously opening of the aperture 42 without contaminating the contents of the vials 26. Although a metal foil was found to be an alternative option, it potentially may occasionally result in the contents of the vials may be contaminated by pieces of foil torn free by the wires 76.

Once operations on the vials 26, eg the relevant cooling or heating conditions have been met, the vials 26 may then be removed for subsequent treatment, examination, characterisation and/or analysis of their contents.

The invention claimed is:

1. Apparatus for parallel dispensing powder samples comprising:
   at least two sample holders for containing powder samples, each said sample holder having a through passage with an axis, the through passage comprising:
      a first aperture through which a powder sample is introduced into said passage,
      a second aperture through which a powder sample flows from said passage,
      flow control means for controlling flow of powder through each said second aperture and into a respective receptacle, and
   an agitator means in each said sample holder for agitating a powder sample during flow of powder through each second aperture,
   wherein said flow control means for each said sample holder comprises a resilient film sealing each said second aperture.

2. Apparatus according to claim 1 wherein each through passage of each sample holder generally tapers from the first aperture to the second aperture thereof.

3. Apparatus according to claim 1 comprising more than two sample holders.

4. Apparatus according to claim 1 wherein said agitator means comprises perforator means for perforating said resilient film and is mounted for axial movement through said passage whereby said film is perforable by it.

5. Apparatus according to claim 1 wherein said agitator means is contactable with a wall defining said passage.

6. Apparatus according to claim 1 wherein said agitator means are each mounted on a common support member reciprocal movement of which relative to a dispense location of said sample holders effects simultaneous reciprocal movement of each agitator means relative to the sample holders.

7. Apparatus according to claim 1 wherein each said agitator means comprises stirrer mechanisms each comprising at least one spring wire mounted for rotation about an axis that aligns substantially coaxially with the axis of each through passage, said at least one wire being mounted in a plane including said axis of rotation.

8. Apparatus according to claim 7 wherein said at least one wire has an unstrained position in which at least a part of the wire is at a radius from said axis that is greater than a radius of the first aperture of the passage of the sample holder and wherein said apparatus further comprises constraint means which in a first position constrains said at least one wire in a strained position in which all of said at least one wire is located at a radius from said axis which is less than the radius of said first aperture and in a second position does not apply any constraint to said at least one wire thereby permitting said at least one wire to move radially outwards towards its unstrained position.

9. Apparatus according to claim 8 wherein said constraint means comprises a pair of parallel plates each having a number of apertures corresponding to a number of stirrer mechanisms, the plates being positioned relative to the stirrer mechanisms such that their planes are normal to the axes of the stirrer mechanisms and, when the apertures of the plates are in registration with one another, a center of each of the apertures is located substantially coaxially with the respective axes of the stirrer mechanisms, the plates being movable relative to one another between a first position, in which the plates are in register with one another and in which the wires of the stirrer mechanisms are in their unstrained position, and a second position, in which the apertures therein are only in partial registration with one another, and in which the wires of the stirrer mechanisms are constrained in their strained position.

10. Apparatus according to claim 9 wherein both plates are movable symmetrically with respect to the axes of the stirrer mechanisms.

11. Apparatus according to claim 7 wherein the stirrer mechanisms have a speed of rotation and/or a vertical reciprocating movement, the speed of rotation of said stirrer mechanisms and/or vertical reciprocating movement of said stirrer mechanisms relative to the sample holder location being controllable to enable the rate of dispensation of the powder samples from the sample holders to be controlled.

12. Apparatus according to claim 1 comprising nozzle means through which a gas flow may be directed into each sample holder through the first apertures thereof.

13. Apparatus according to claim 1 comprising gas inlet means for directing a gas flow at an external lower wall of each sample holder.

14. Apparatus according to claim 1 comprising gas outlet means for venting gas from the vicinity of an external lower wall of each sample holder.

* * * * *